United States Patent [19]

Williams et al.

[11] Patent Number: 5,118,858
[45] Date of Patent: Jun. 2, 1992

[54] TRIPHENYL METHANETHIOL-35S

[75] Inventors: Haydn W. R. Williams, Dollard Des Ormeaux; Robert N. Young, Senneville; Robert J. Zamboni, Longueuil, all of Canada

[73] Assignee: Merck Frosst Canada, Inc., Kirkland, Canada

[21] Appl. No.: 601,157

[22] Filed: Oct. 19, 1990

Related U.S. Application Data

[63] Continuation of Ser. No. 318,402, Mar. 2, 1989, abandoned.
[51] Int. Cl.$^5$ .............................................. C07C 321/06
[52] U.S. Cl. ..................................... 568/67; 546/175; 560/15; 564/162; 568/68
[58] Field of Search .......................................... 568/67

[56] References Cited

PUBLICATIONS

Journal of Labelled compounds and radiopharmaceuticals, vol. XXV, No. 10 1988, P. Egli and Bruce H. Migdalof, "Synthesis of Captopril Labeled with $2_H$, $3_H$, $^{14}C$ or $^{35}S$".

*Primary Examiner*—Mary C. Lee
*Assistant Examiner*—Robert C. Whittenbaugh
*Attorney, Agent, or Firm*—Mark R. Daniel; Joseph F. DiPrima

[57] ABSTRACT

Disclosed herein are /$^{35}$S/-labelled compound of the formula (I):

$$(C_6H_5)_3C^{35}SH$$

and processes therefor. This Compound (I) is useful as an intermediate for the introduction of sulfur isotope into a variety of compounds. For example, it is useful in the introduction of sulfur isotope into important compounds such as 6-mercaptopurine, 5-[3-(2-(7-chloroquinolin-2-yl)ethenyl)phenyl]-8-dimethylcarbamyl-4,6-dithioactanoic acid, a potent antagonist of leukotriene D$_4$; thiophosphoric acid derivatives, photoaffinity reagents and the like.

1 Claim, No Drawings

TRIPHENYL METHANETHIOL-35S

This is a continuation of application Ser. No. 07/318,402, filed Mar. 2, 1989 now abandoned.

BACKGROUND OF THE INVENTION

In order to carry out biochemical studies of certain compounds such as 5-[3-(2-(7-chloroquinolin-2-yl)-ethenyl)phenyl]-8-dimethylcarbamyl-4,6-dithiooctanoic acid (also known as L-660,711) a potent antagonist of leukotriene D4(LTD4) on the LTD4 receptor, it is desirable to prepare the antagonist with high intrinsic radioactivity. The introduction of a $^{35}S$ atom appears to be an attractive way to fulfilling this requirement. Prior art compounds such as $C_6H_5CH_2{}^{35}SH$ described by Gemeiner et al in Chem. Abs. 86: 157295Y(1977), 99: 7012h(1983), 100 193798f (1984) or those of the formula; $O_2N—C_6H_5—CH_2{}^{35}SH$ described by Watabe et al in Chem. Abs. 103, 191021K are difficult to use for this purpose because they are more difficult to de-block.

$H_2{}^{35}S$ has also been used as starting materials for introducing a sulfur radioisotope into same molecules. However, it being gaseous, is hazardous and difficult to use. In addition, it suffers from the drawback of having two reactive hydrogens which can cause problems in small scale reactions.

As to the method of preparation, Boscato et al described methods for the incorporation of elemental sulfur into organic compounds. See Tetrahedron Letters 21 1519 1520 (1980). The reaction may be represented by the scheme:

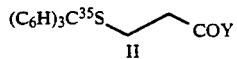

SUMMARY OF THE INVENTION

The present invention relates to triphenylmethanethiol-$^{35}S$ of the formula (I):

$(C_6H_5)_3C^{35}SH$ and process therefor. This compound is useful as an intermediate for the introduction of sulfur isotope into a variety of compounds including but not limited to the aforementioned L-660,711, thiophosphoric acid derivatives, 6-mercaptopurine, photo-affinity reagents and the like.

Included within the scope of this invention are derivatives of Compound I such as:

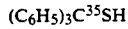

in which Y is NMe2 or OMe etc. and $^{35}S$ labelled L,660,711 (III).

Compound (I) is relatively involatile and contains only one reactive hydrogen. It is therefore safer and easier to use than the prior compound $H_2{}^{35}S$ described above as a reagent. Furthermore, the trityl groups would act as a protecting group if further reactions are necessary to get to the end products.

DETAILED DESCRIPTION OF THE INVENTION

According to the present invention, Compound I is prepared by two methods.

In the first method, triphenylmethanol is treated with $H_2{}^{35}S$ and trifluoroacetic acid at room temperature. The trifluoroacetic acid is then evaporated yielding $(C_6H_5)_3C^{35}SH$ which is in turn treated with acetontrile, N,N-dimethylacrylamide and 1,8-diazabicyclo[5,4.0]undec-7-ene or with a lower alkyl ester of acrylic acid yielding Compound II. The foregoing reaction may be illustrated by the following scheme:

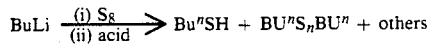

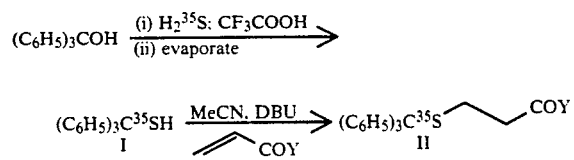

in which Y is NMe2, OMe and the like.

The second method which is the preferred method for the preparation of (I), involves the treatment of triphenylmethane with n-butyllithium in an etheral solvent such as tetrahydrofuran. The resultant solution is reacted with $^{35}S$, and then treated with a reducing agent to reduce any disulfide and neutralized with trifluoroacetic acid. The solvent is evaporated yielding Compound I. The reaction may be represented by the following scheme:

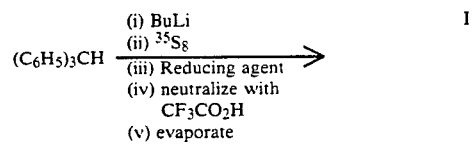

It is advantageous to include a small amount of a reducing agent such as tri-n-butyl-phosphine in the reaction of triphenylmethane with n-butyl-lithium.

Once comopund I is obtained as described, it can be readily treated to yield those compounds as described in the first method.

Compound I is useful as an intermediate for the introduction of $^{35}S$ atom into other organic molecules via Michael addition. For example: The reactions with acrylic acid derivatives described above.

In addition compound I can be used for the displacement of a halogen atom in the presence of a base with or without the aid of a catalytic amount of copper such as:

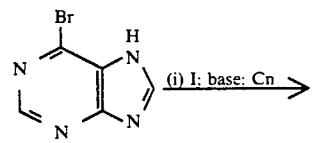

-continued

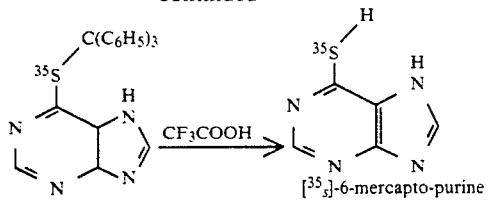

For the preparation of III, the reaction is as follows:

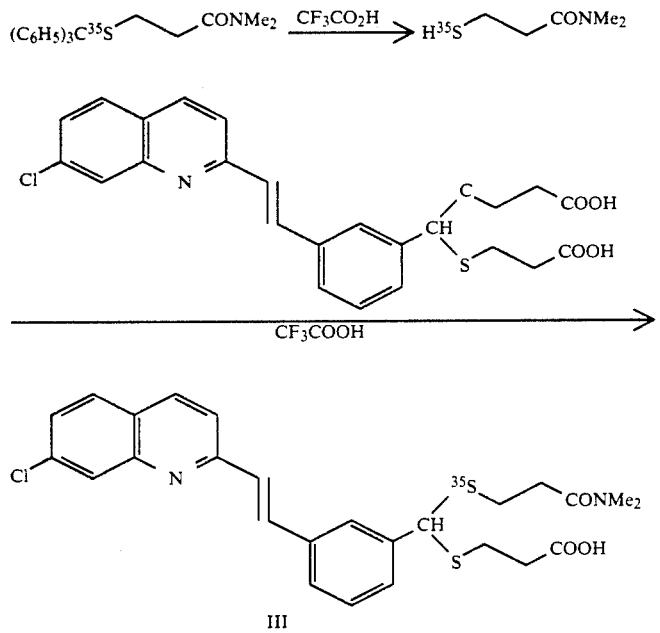

As can be readily appreciated by those skilled in the art, instead of the trityl group in I, other radicals such as:

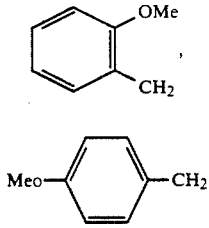

t-butyl can also be advantageously employed.

The following examples are illustrative of the present invention. All temperatures are in degrees centigrade and room temperature denotes about 15° to 20° C.

INSTRUMENTATION

Infrared spectra were recorded using a Perkin Elmer 683 spectrophotometer, and proton magnetic resonance spectra were obtained using a Bruker EM250 instrument with tetramethysilane as internal standard. High pressure liquid chromatography was performed with Waters equipment.

EXAMPLE 1

N,N-Dimethyl-3-triphenylmethylthiopropanoamide

To a mixture of N,N-dimethylacrylamide (515 uL, 5.0 mmol), triphenylmethanethiol (1.38 g, 5.0 mmol) and acetonitrile (2.0 mL) was added 1,8-diazabicycloundec-7-ene (DBU) (75 Ul, 0.5 mmol) initiating a rapid reaction, and giving a pale reddish-brown solution from which the product crystallized. The solid was collected, and washed with a little acetonitrile 1.42 g (76%). On recrystallization from acetonitrile, the amide had mp 114°–116° C. IR v max (KBr) 1647 cm$^{-1}$. $^1$HNMR δ7.43(t, 6H), 7.24 (m, 9H), 2.87(S, 3H), 2.78(S, 3H), 2.55(t, 2H), 2.15(t, 3H).

Anal. $C_{24}H_{25}NOS$ requires: C 76.76, H 6.71, N 3.73, S 8.54; found: C 77.08, H 6.81, N 3.76, S 8.75.

EXAMPLE 2

N,N-Dimethyl-3-triphenylmethylthiopropanoamide

First Procedure

A Kontes hydrolysis tube of about 1 mL capacity was charged with triphenylmethanol (26 mg, 0.1 mmol), and the air in the tube was swept out with hydrogen sulfide. Trifluoroacetic acid (200 µL) was added, and the tube was sealed. The reaction mixture was shaken occassionally, and after 30 minutes the trifluoroacetic acid was evaporated in a stream of nitrogen. Final traces of trifluoroacetic acid were removed under vacuum, then acetonitrile (200 µL), N,N-dimethylacrylamide (10 µL), and DBU (25 µL) were added. After a reaction time of 30 minutes, the solvent was evaporated in a stream of nitrogen.

Estimation of the product in the residual oil can be performed by dissolving the oil in ethyl acetate (10 mL), and carrying out high pressure liquid chromatography (hplc) using a solution of authentic product from Example 1 as a standard. Suitable hplc conditions employ a 7.8 mm×30 cm silica gel column eluted at 3.0 mL/minute with 1:3 ethyl acetate/hexane.

The u.v. detector is set at 270 nm. The retention time of the product is about 4.9 minutes, and the yield is typically 40%.

The above procedure is amenable to adaption for the preparation of [$^{35}$]-N,N-dimethyl-3-triphenylmethylthiopropanoamide by replacing hydrogen sulfide with [$^{35}$]-hydrogensulfide with a specific activity of about 1300 Curies/mmol to provide a product of about the same activity, and replacement of N,N-dimethylacrylamide with a lower alkyl acrylate in the above procedure provides an alkyl [$^{35}$S]-3-triphenylmethylthiopropanoate.

EXAMPLE 3

N,N-Dimethyl-3-triphenylmethylthiopropanoamide

Second Procedure

To a solution of triphenylmethane (27 mg, 0.11 mmol) in dry tetrahydrofuran (250 μL), contained in an argon-filled 1 mL Reactivial sealed with a septum, 1.6M butyllithium in hexane (60 μL) was added by syringe. The mixture was stirred at room temperature for 5 minutes, then it was withdrawn into a syringe containing a few μL of dry tetrahydrofuran, and transferred into another argon-filled reaction vessel containing sulfur (1.1 mg, 0.034 mmol). This mixture was stirred at room temperature for 10 minutes, tri-n-butylphosphine (3 μL) was added, and the reaction mixture was neutralized with trifluoroacetic acid (9 μL). After evaporation of the solvent in a stream of nitrogen, acetonitrile (100 μL), N,N-dimethylacrylamide (5 μL), and DBU (10 μL) were added in succession. The mixture was stirred at room temperature for 30 minutes, and the work-up and estimation of the product was performed as in Example 2. The yield is typically 50% based on the amount of sulfur used.

This procedure too can be adapted for the preparation of [$^{35}$S]-labelled propanoic acid derivatives by using the radioactive isotope of sulfur of atomic weight 35, and either N,N-dimethylacrylamide, or a lower alkyl ester of acrylic acid as the reactants. The eluants containing the labelled product is evaporated in a stream of nitrogen, and the residue is dissolved in a 1 mM solution of 2,6-di-t-butyl-4-crecol in ethanol.

EXAMPLE 4

[6-$^{35}$S]-5-[3-{2-(7-Chloroquinolin-2-yl)ethenyl}-phenyl]-8-dimethylcarbamyl-4,6-dithiaoctanoic acid III To a nitrogen-filled Reactivial (volume 300 μL) containing 5-[3-{2-(7-chloroquinolin-2-yl)-ethenyl}phenyl]-4,6-nonanedioic acid (ca. 0.2 mg) was added a solution of 3-mercaptopropanoic acid (8 μg) in ether (10 μL), and then the ethanol solution (II, from Example 2 or 3) of the labelled reagent (140, μL, ca. 200 μCi). Then solvents were evaporated in a stream of nitrogen, then trifluoroacetic acid (50 uL) was added. The reaction mixture was allowed to stand for 1 hour, and then the trifluoroacetic acid was evaporated in a stream of nitrogen. For injection into the HPLC apparatus the residue was dissolved in the HPLC solvent, (this neutralizes the remaining trifluoroacetic acid as can be seen by the fading of the yellow colour of the mixture). HPLC was performed using a 7.8 mm×30 cm $C_{18}\mu$ Bondapak column eluted at 7.0 ml/min with 165:95 methanol/water containing 1 g/L of sodium dihydrogen phophate neutralized to pH 6.5 with ammonium hydroxide, and 0.01% each of mercaptoethanol and dithioerythritol. For establishing the elution time of "cold" L-660,711, the UV detector was set at 280 nm. The elution time was adjusted to 5 to 6 minutes by the addition of a little methanol or water to the elution solvent prior to the preparative run. In the vicinity of the expected elution time, fractions were collected at 20 second intervals. Scintillation counting of the fractions indicated which fractions contained product, and these were pooled. Evaporation of these fractions in a stream of nitrogen was taken only as far as the removal of the methanol, then the solution was diluted with water containing 0.01% of mercapto ethanol, and 0.01% of dithioerythritol, and this solution was passed through a $C_{18}$ Sep Pak, which resulted in 100% retention of the radioactivity. On washing through the Sep Pak with methanol (2 mL aliquots), all of the radioactivity was eluted in the first two fractions which were combined and evaporated in nitrogen. This material was purified a second time by HPLC, and the resulting product was pure by analytical HPLC, both from the point of UV absorption and radioactivity. The yield was 35 μCi.

What is claimed is:

1. A compound of the formula:

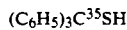

$(C_6H_5)_3C^{35}SH$

* * * * *